(12) United States Patent
Little et al.

(10) Patent No.: US 6,306,129 B1
(45) Date of Patent: Oct. 23, 2001

(54) CRYOSURGICAL SYSTEM AND METHOD

(75) Inventors: William A. Little, Palo Alto; Igor Sapozhnikov, San Jose; Todd Thompson, Pleasanton; George M. Savage, Portola Valley, all of CA (US)

(73) Assignee: Femrx, Inc., Sunnyvale, CA (US)

(\*) Notice: Subject to any disclaimer, the term of this patent is extended or adjusted under 35 U.S.C. 154(b) by 0 days.

(21) Appl. No.: 09/377,377

(22) Filed: Aug. 19, 1999

Related U.S. Application Data (63) Continuation of application No. 09/087,113, filed on May 28, 1998, now abandoned.
(60) Provisional application No. 60/059,449, filed on Sep. 22, 1997.

(51) Int. Cl.[7] ................................................ A61B 18/18
(52) U.S. Cl. ...................................... 606/23; 128/DIG. 27
(58) Field of Search ........................ 606/20–26; 607/105, 607/113; 128/DIG. 27

(56) References Cited

U.S. PATENT DOCUMENTS

| | | |
|---|---|---|
| 3,272,203 | 9/1966 | Chato . |
| 3,273,356 | 9/1966 | Hoffman . |
| 3,298,371 | 1/1967 | Lee . |
| 3,398,738 | 8/1968 | Lamb et al. . |
| 3,401,533 | 9/1968 | Maybury . |
| 3,431,750 | 3/1969 | LeFranc . |
| 3,439,680 | 4/1969 | Thomas, Jr. . |
| 3,477,434 | 11/1969 | Hood, Jr. et al. . |
| 3,536,075 | 10/1970 | Thomas . |
| 3,662,755 | 5/1972 | Rautenbach et al. . |
| 3,859,986 | 1/1975 | Okada . |
| 3,889,680 | 6/1975 | Armao . |
| 3,913,581 | 10/1975 | Ritson et al. . |
| 3,924,628 | 12/1975 | Droegemueller et al. . |
| 4,015,606 | 4/1977 | Mitchiner et al. . |

(List continued on next page.)

FOREIGN PATENT DOCUMENTS

| | | |
|---|---|---|
| WO 83/03961 | 11/1983 | (WO) . |
| WO 93/08751 | 5/1993 | (WO) . |
| WO 98/06985 | 2/1998 | (WO) . |

OTHER PUBLICATIONS

Little, W.A. "Advances in Joule–Thomson cooling," (1990) Advances in Cryogenic Engineering, vol. 35, pp. 1305–1314.

(List continued on next page.)

*Primary Examiner*—Linda C. M. Dvorak
*Assistant Examiner*—R. Kearney
(74) *Attorney, Agent, or Firm*—Verne E. Kreger, Jr.

(57) ABSTRACT

A cryosurgical system comprises a compressor unit and a probe assembly. A secondary refrigerant stream from the compressor unit pre-cools a heat exchanger within the probe assembly in a standby mode of operation. After the heat exchange is pre-cooled, a primary refrigerant stream can be passed through the cooled heat exchanger and thereafter expanded within a tissue-contacting portion of the probe assembly to achieve very low temperatures, typically minus 100° C. or lower. After cooling, the refrigerant stream may be passed through the probe assembly with no or partial expansion to warm the tissue-contacting surface of the probe. A probe sheath can be used to provide sterility.

10 Claims, 11 Drawing Sheets

U.S. PATENT DOCUMENTS

| | | |
|---|---|---|
| 4,207,897 | 6/1980 | Lloyd et al. . |
| 4,377,168 | 3/1983 | Rzasa et al. . |
| 4,764,845 | 8/1988 | Artus . |
| 4,781,033 | 11/1988 | Steyert et al. . |
| 4,829,785 | 5/1989 | Hershey . |
| 4,840,043 | 6/1989 | Sakitani et al. . |
| 4,844,073 | 7/1989 | Pohler . |
| 4,875,346 | 10/1989 | Jones et al. . |
| 4,951,471 | 8/1990 | Sakitani et al. . |
| 4,990,412 | 2/1991 | Hersey . |
| 5,063,747 | 11/1991 | Jones et al. . |
| 5,078,713 | 1/1992 | Varney . |
| 5,101,894 | 4/1992 | Hendricks . |
| 5,139,496 | 8/1992 | Hed . |
| 5,147,355 | 9/1992 | Friedman et al. . |
| 5,157,938 | 10/1992 | Bard et al. . |
| 5,207,674 | 5/1993 | Hamilton . |
| 5,275,595 | 1/1994 | Dobak, III . |
| 5,281,212 | 1/1994 | Savage et al. . |
| 5,281,213 | 1/1994 | Milder et al. . |
| 5,281,215 | 1/1994 | Milder . |
| 5,281,217 | 1/1994 | Edwards et al. . |
| 5,324,286 | 6/1994 | Fowle . |
| 5,337,472 | 8/1994 | Longsworth . |
| 5,365,750 | 11/1994 | Greenthal . |
| 5,400,602 | 3/1995 | Chang et al. . |
| 5,403,309 | 4/1995 | Coleman et al. . |
| 5,423,807 | 6/1995 | Milder . |
| 5,494,039 | 2/1996 | Onik et al. . |
| 5,501,681 | 3/1996 | Neuwirth et al. . |
| 5,520,682 * | 5/1996 | Baust et al. ............................ 606/24 |
| 5,595,065 | 1/1997 | Boiarski et al. . |
| 5,617,739 | 4/1997 | Little . |
| 5,632,743 | 5/1997 | Clarke . |
| 5,644,502 | 7/1997 | Little . |
| 5,647,868 | 7/1997 | Chinn . |
| 5,667,505 | 9/1997 | Straus . |
| 5,674,218 | 10/1997 | Rubinsky . |
| 5,741,248 * | 4/1998 | Stern et al. ............................ 606/21 |
| 5,758,505 * | 6/1998 | Dobak, III et al. ....................... 62/6 |
| 5,800,488 * | 9/1998 | Crockett ............................... 607/105 |
| 5,910,104 * | 6/1999 | Dobak, III et al. .................. 600/121 |
| 6,106,518 * | 8/2000 | Wittenberger ........................ 606/23 |

OTHER PUBLICATIONS

Little, W.A. "Microminiature Refrigerators of Joule–Thomson Cooling of Electronic Chips and Devices," (1990) Advances in Cryogenic Engineering, vol. 35, pp. 1324–1333.

Kleemenko, A.P. "One flow Cascatde Cycle (in Schemes of Natural Gas Liquefaction and Separation)," (1959) Proceedings at Intl. Congress of Refrig. Copenhagen, vol. 1, pp. 34–35.

Grokhol'skii et al., "Cryogenic Dental system Cryoelectronica–1'," Medicinskaya tekhnika (Medical Technology) pp. 16–20 (No. 3, May–Jun. 1982).

Kobrianski et al., "A Cryomedical Device B ased on a Closed–Cycle Joule–thomson Cooling systgem," Elektronnaya Promyslennost (Electronics Industry) pp. 71–72 No. 8–9, 1979.

Gassanov et al., "Experience with the Development and Use of Cryogenic surgical Equipment," Elektronnaya Promyslennost (Electronics Industry), pp. 41–42 No. 1, 1987.

* cited by examiner

CRYOSURGICAL SYSTEM AND METHOD

CROSS-REFERENCE TO RELATED APPLICATION

This application is a continuation of Ser. No. 09/087,113, filed on May 28, 1998, now abandoned, which claimed benefit of U.S. Provisional Application No. 60/059,449, filed on Sept. 22, 1997, the full disclosure of which is incorporated herein by reference.

BACKGROUND OF THE INVENTION

1. Field of the Invention

The present invention relates generally to systems and methods for performing cryosurgery. More particularly, the present invention relates to use of a closed refrigeration system for cooling a surgical probe to very low temperatures in an efficient and rapid fashion.

Cryosurgery has been used for a number of years for the treatment and ablation of tissue for a variety of therapeutic purposes. For example, cryosurgical probes have been used for ablation of the endometrial lining of the uterus for the treatment of bleeding and other disorders. Most cryosurgical systems rely on either liquid nitrogen or nitrous oxide as a coolant medium. Liquid nitrogen is advantageous since it can achieve very low temperatures, but requires extensive insulation in order to protect the patient and physician from the liquid nitrogen while it is being introduced to the treatment site. Moreover, since the liquid nitrogen is evaporated and released into the atmosphere, continual replenishment of the liquid nitrogen source is necessary. Nitrous oxide is advantageous since it can be delivered at room temperature, thus reducing the requirement for insulation, and be cooled at the treatment site by Joule-Thomson expansion. The temperatures achieved by nitrous oxide expansion, however, are not nearly as low as those achieved with liquid nitrogen, and the use of nitrous oxide also suffers from the need for continual replenishment.

An improvement over the use of liquid nitrogen and nitrous oxide is proposed in U.S. Pat. No. 5,275,595 to Dobak, III. In particular, it is proposed that a closed refrigeration system be employed together with a counter-current heat exchanger in the probe of a cryosurgical device. The patent asserts that use of particular refrigerant gas mixtures can achieve very low temperatures suitable for many forms of cryosurgery.

The system of Dobak, III, however, suffers from a number of disadvantages. In particular, use of the counter-current heat exchanger shown in the patent requires that system equilibrium be established before the lowest system temperatures can be achieved. Thus, the system must be running for some time before useful temperatures can be achieved. Second, the system of Dobak, III provides no means for warming the probe after it has been cooled. Many forms of cryosurgery benefit from repeated heat/thaw cycles, where the ability to heat the probe between successive cool cycles would be desirable. Further, Dobak, III proposes a probe having vacuum insulation over its exterior. The vacuum insulation, however, is shown to be on the probe only and will thus have a relatively small total volume, i.e., the volume is limited to the annular space between the coaxial members that make up the probe. Vacuum insulation in this and other systems with such low volumes suffer excessively from out-gassing (since the internal surface area from which the gas evolves is large compared to the volume available to accommodate the gas) which can lessen or destroy the insulating capability. Finally, Dobak, III proposes no means for sterilizing the probe system. The probe and compressor of Dobak, III will presumably be a closed, sealed system. The sterilization of the probe in such a system will be problematic.

For these reasons, it would be desirable to provide improved closed refrigeration systems for performing cryosurgery. In particular, it would be desirable to provide cryosurgical refrigeration systems which can be pre-cooled in a standby mode prior to use. Full probe cooling from the standby mode will preferably be achieved within several minutes or less, under thermal load. It would further be desirable to provide cryosurgical refrigeration systems which can heat the tissue-contacting probe surface between successive cooling cycles. More preferably, the ability to heat the probe will be achieved using components of a refrigeration system which are already available. Moreover, it will be desirable to provide closed cryosurgical refrigeration systems where sterilization of the probe components of such systems is facilitated, or the need to sterilize the probes is eliminated. Still further, it would be desirable to provide vacuum-insulated cryosurgical probes which are less prone to out-gassing and loss of vacuum insulation. At least some of these objectives will be met by different aspects of the present invention.

2. Description of the Background Art

U.S. Pat. No. 5,275,595 describes a cryosurgical probe which is cooled by a refrigeration system. U.S. Pat. Nos. 5,644,502 and 5,617,739 describe refrigerants and refrigeration systems of a type which could be employed as a part of the systems of the present invention. Cryosurgical treatment of the uterine endometrium and often other tissue is described in a number of patents and medical publications, including U.S. Pat. Nos. 5,647,868; 5,520,682; 5,501,681; 5,403,309; 5,400,602; 5,494,039; 5,207,674, 5,139,496; 3,924,628; and 3,889,680. Other cooled medical probes are described in U.S. Pat. Nos. 4,844,073; WO 93/06985; WO 93/08951; and WO 83/03961. Use of particulate microcrystalline material, e.g. diamond suspended in a fluorocarbon or paraffin, as a heat transfer material is described in U.S. Pat. No. 4,764,845.

The use of multi-component gas mixtures in compressor systems is described in Kleemenko (1959) *Proc.* 10th. Intl. *Congress of Refrigeration*, Copenhagen 1:34–39, Pergamon Press, London; Little (1990) Adv. Cry. Engineering 35:1305–1314 and 1325–1333.

SUMMARY OF THE INVENTION

Systems according to the present invention comprise a compressor which produces a recirculating refrigerant stream. The compressor may comprise any conventional system, but will preferably comprise systems according to the teachings of U.S. Pat. Nos. 5,644,502, and 5,617,739, the full disclosures of which are incorporated herein by reference. In addition to such compressors, the systems of the present invention will comprise a probe assembly having a tissue-contacting surface and a primary expansion orifice. The probe is connected to the compressor to receive high pressure refrigerant and to pass said high pressure refrigerant through the primary expansion orifice. Such expansion produces cooling of the tissue-contacting surface and results in low pressure cooled refrigerant which is returned to the compressor.

In a first aspect, the system of the present invention will further comprise means for selectively circulating a warm fluid typically refrigerant from the compressor, through the probe to warm the tissue-contacting surface, usually between successive cooling cycles. The warm fluid circulating means typically comprises conduit from the compressor to the probe for passing, but not expanding or only partially expanding a portion of the recirculating refrigerant stream past the tissue-contacting surface. The warm refrigerant may be at or slightly above or below room temperature, but will preferably be well above the typical operating temperatures of the probe for cryosurgery. Usually, the warm refrigerant will be above 0° C., preferably being above 10° C., often being above 20° C., or higher. Usually, the system of the present invention will include a controller to direct passage of a high pressure refrigerant from the compressor to the primary expansion orifice in order to stop active cooling and then initiate flow of the warm refrigerant in order to start warming of the tissue-contacting surface of the probe.

In a second aspect, the system of the present invention will comprise a heat exchanger disposed to pre-cool at least a portion of a primary stream of the recirculating refrigerant which is being directed to the probe for expansion and cooling of the tissue-contacting surface. Means will further be provided for pre-cooling the heat exchanger prior to passing the primary probe refrigerant stream therethrough. In the exemplary embodiment, the pre-cooling means comprises a separate refrigeration loop from the compressor and through a secondary expansion orifice in the heat exchanger. The heat exchanger is upstream and isolated from the tissue-contacting surface of the probe, so the heat exchanger can be cooled to low temperatures without affecting the temperature of the tissue-contacting surface of the probe. As described in more detail below, the heat exchanger will usually be in a vacuum enclosure which acts to insulate the heat exchanger, in addition to its being isolated from the tissue-contacting surface. Thus, the heat exchanger can be pre-cooled by expanding a secondary stream or portion of the recirculating refrigerant through the secondary expansion orifice and passing the resulting cooled, expanded refrigerant through the heat exchanger, typically until a temperature below minus 60° C. is achieved. The primary refrigerant stream may then be directed through the heat exchanger, where it is pre-cooled to a target temperature, in the range from minus 10°C. to minus 110°C., typically minus 60° C., prior to expansion in the probe tip adjacent to the tissue-contacting surface. By pre-cooling the refrigerant, very low temperatures, typically below minus 100°C., can thus be achieved at the tissue-contacting surface of the probe. As a particular benefit, the probe tip can be cooled from room temperature to these very low temperatures very quickly, i.e., within several minutes.

Preferably, the heat exchanger and the probe are present in a common, hand-held assembly and connected to a separate compressor unit through a flexible connector. The heat exchanger preferably comprises a coiled shell with one or more coiled inner tube(s). The high pressure refrigerant passes through the inner tube(s) in a direction toward the probe, and the expanded pre-cooling refrigerant stream passes in the opposite direction in an annular space between the inner tube and the shell. The coil geometry is advantageous since it allows relatively long lengths for the countercurrent heat exchanger to be incorporated into small cylinders.

In another aspect, the system of the present invention further comprises a sheath adapted for removable placement over the probe. The sheath can be disposable and thus eliminate the need for sterilization of the probe or any other portion of the compressor/probe system. Placement of a sheath over cryogenic probes has generally been avoided because of loss of heat-transfer efficiency, but the highly efficient refrigeration systems of the present invention at least in part obviate that concern. Moreover, the heat transfer is improved in the systems of the present invention by providing a heat conductive material between an exterior surface of the probe and an interior surface of the sheath. A preferred heat conductive material comprises a heat conductive powder, such as a diamond or graphite powder, suspended in a liquid carrier. By using such heat conductive materials, typically together with minimum clearance between the probe exterior and sheath interior, usually less than 0.15 mm, adequate heat transfer rates can be achieved.

In yet another aspect, the system of the present invention comprises a vacuum enclosure extending over all exterior portions of the probe except for the tissue-contacting surface. Preferably, the vacuum enclosure will cover not only the probe but also the heat exchanger which is connected to the probe. As the heat exchanger will generally have a much larger volume than the probe, the combined volumes of the probe interior and the heat exchanger lessen problems (vacuum degradation) which result from out-gassing of very small probe vacuum volumes.

The present invention further provides methods comprising recirculating a refrigerant from a compressor through a probe and expanding the refrigerant to cool a surface of the probe. The cooled surface is then contacted against tissue for a variety of cryosurgical procedures, such as ablation of the uterine endometrial lining.

In a first aspect, the method of the present invention further comprises circulating a warm fluid from the compressor through the probe to warm the tissue-contacting surface after it has been cooled. Preferably, the warm fluid comprises a portion of the recirculating refrigerant which is passed through the probe without expansion. Usually, the warm fluid will not pass through the heat exchanger in order to avoid warming the heat sink therein.

In another aspect, the method of the present invention further comprises pre-cooling a heat exchanger connected to the probe prior to expanding the primary refrigerant. The primary refrigerant is then passed through the pre-cooled heat exchanger prior to expansion in the probe in order to enhance cooling. Usually, the pre-cooling step comprises passing a secondary stream of the refrigerant through an expansion orifice and directing the cooled, expanded refrigerant through the heat exchanger. Also preferably, the heat exchanger is cooled to a temperature of minus 30° C. or below, often minus 60° C. or below, prior to passing the probe refrigerant therethrough. Still more preferably, these methods result in a probe which is cooled to a temperature of minus 100°C. or below.

In yet another aspect, the method of the present invention further comprises covering the probe with the sheath prior to contacting the cooled surface against tissue.

Preferably, a heat conductive material is placed between an outer surface of the probe and an inner surface of the sheath to enhance heat transfer. Still more preferably, the heat conductive material comprises a heat conductor powder suspended in a liquid carrier. Optionally, a heat conductive liquid, gel, or other material, can be used to coat, fill, or otherwise occupy at least a portion of the uterus or other body cavity being treated. Preferably, the material will not freeze at the expected treatment temperature and will conform to both the probe and the uterine wall for maximum heat transfer therebetween.

BRIEF DESCRIPTION OF THE DRAWINGS

FIG. 2 is an exploded view of a cryosurgical probe of the system of. FIG. 1.

DESCRIPTION OF THE SPECIFIC EMBODIMENTS

Figure 1:
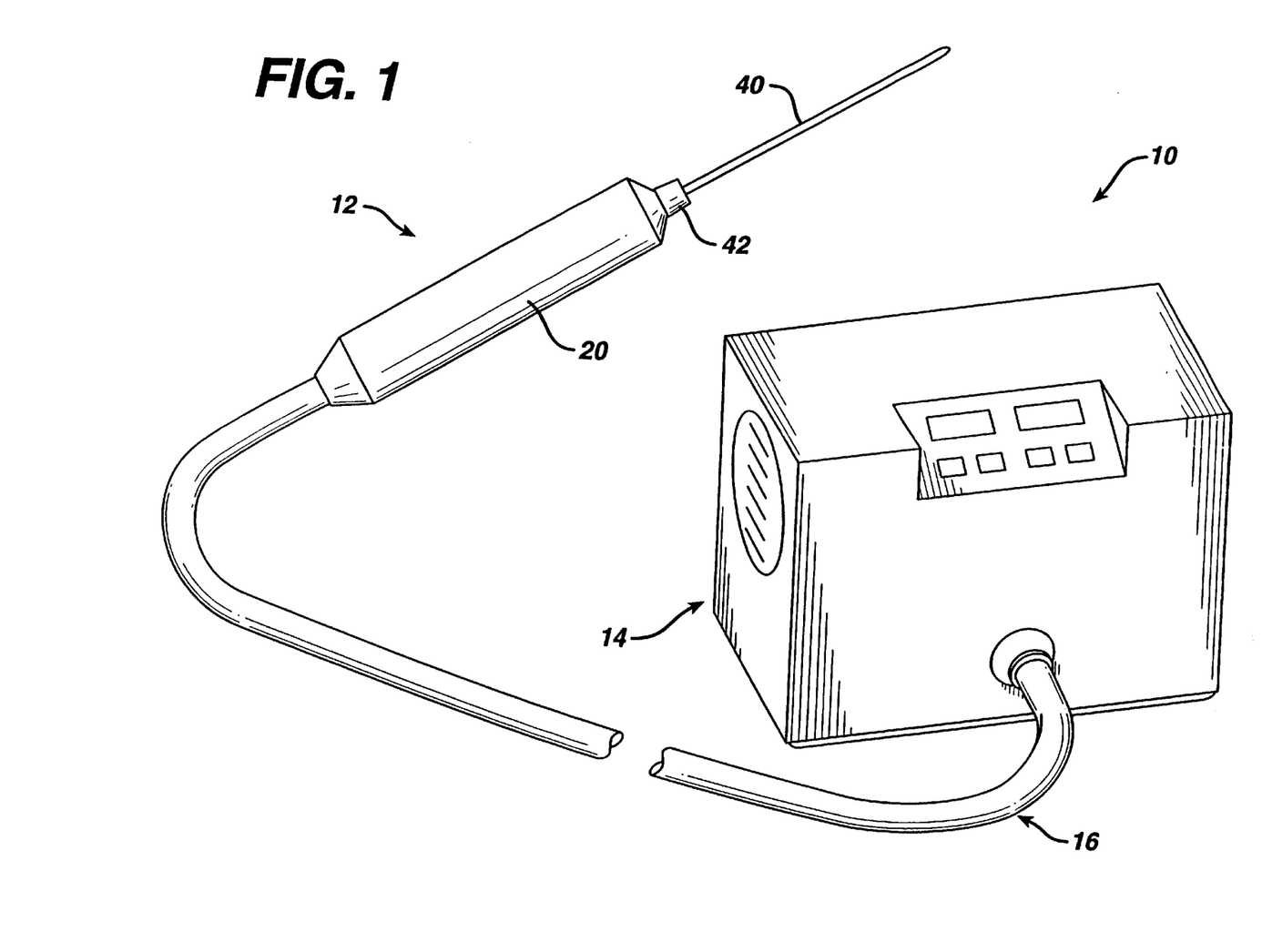
FIG. 1 illustrates a system constructed in accordance with the principles of the present invention.

Referring to FIG. 1, a cryosurgical system 10 constructed in accordance with the principles of the present invention comprises a probe assembly 12 connected to a compressor 14 by a flexible umbilical tube 16. The compressor 14 will include a reservoir of refrigerant, a compressor, valving, and digital and analog control circuitry for controlling the mechanical components to produce up to three recirculating refrigerant streams, as described in more detail below. The refrigerant streams will be directed from the compressor 14 to the probe assembly 12 through individual conduits within the umbilical tube 16. Generally, all streams flowing through the umbilical tube 16 will be at or close to room temperature, minimizing the need for insulation of the tube. Details of the refrigerant flows will be described hereinafter.

Figure 2:
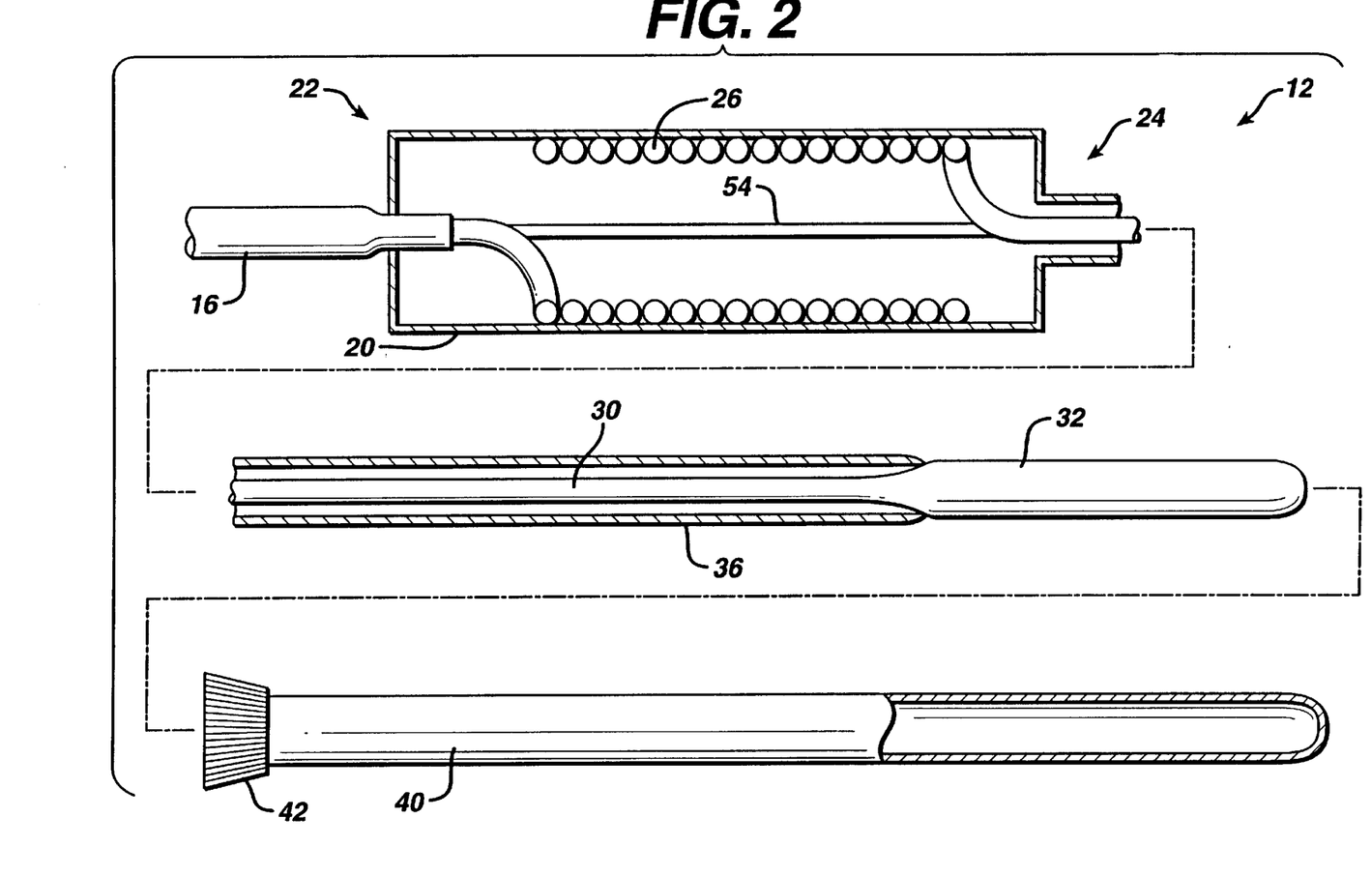
Figure 3:
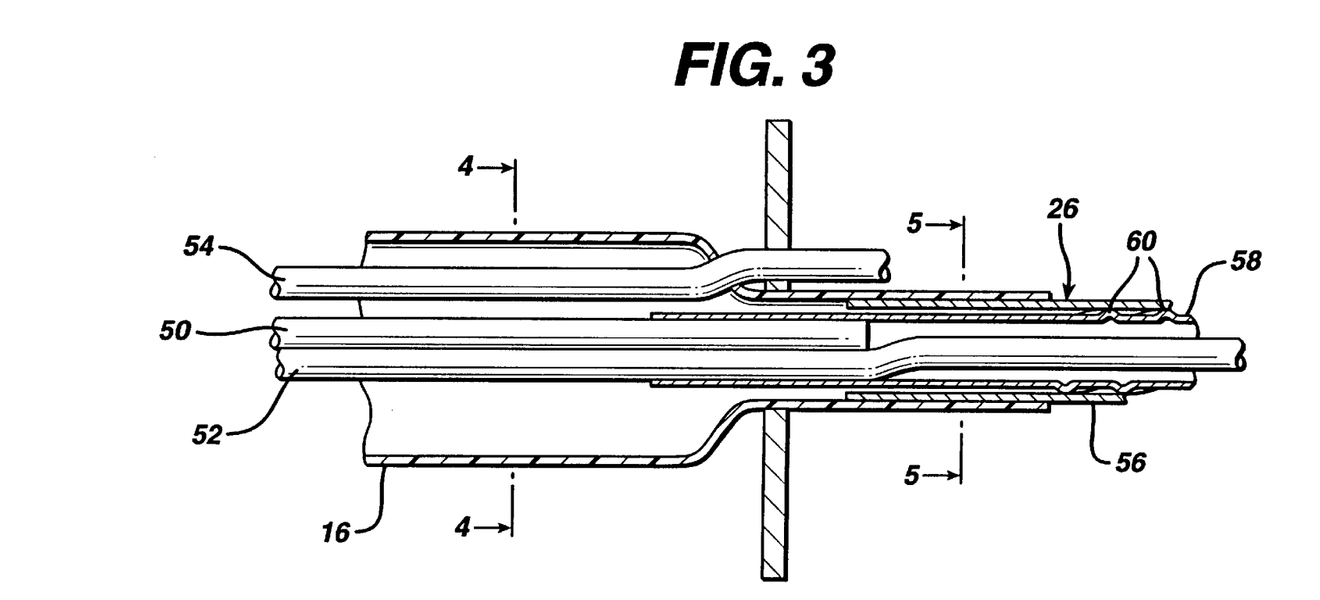
FIG. 3 is a detailed, cross-sectional view of a proximal end of a heat exchanger incorporated into the probe of FIG. 2.
Figure 4:
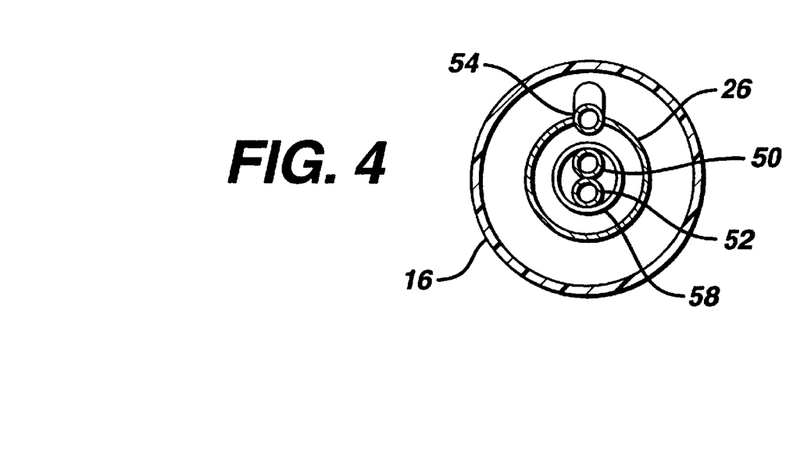
FIG. 4 is a cross-sectional view taken along line 4–4 of FIG. 3.
Figure 5:
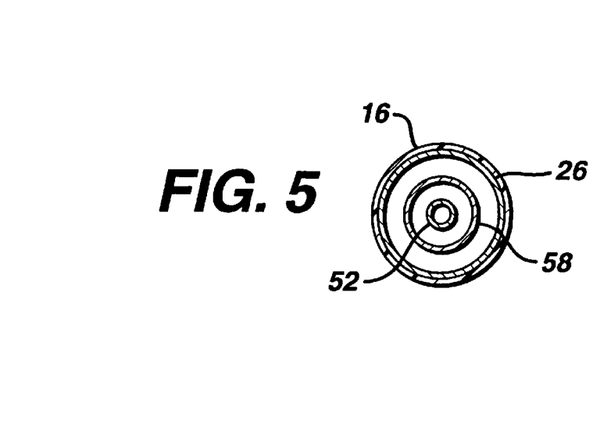
FIG. 5 is a cross-sectional view taken along line 5–5 of FIG. 3.

The probe assembly 12 is best illustrated in FIG. 2 and includes a canister or vacuum enclosure 20 having a proximal end 22 and distal end 24. The umbilical tube 16 enters the canister through its proximal end 22 and is connected to a helical heat exchanger 26, as will be described in greater detail in connection with FIG. 3 below. The tube which comprises the helical heat exchanger 26 continues distally out through distal end 24 of the canister 20, identified at reference numeral 30. The tube 30 expands at its distal end 32, typically having a diameter of about 3 mm to 8 mm and a length of about 2 cm to 7cm.

Tubular extension 36 or vacuum enclosure extension of the canister 20 extends over a major portion of the length of the probe extension 30, typically covering 15 cm to 30 cm. Tubular extension 36 is open to the interior of canister 20, and preferably a vacuum will be held and sealed within the combined interiors of the canister and the tubular extension. Such vacuum provides good insulation of both the heat exchanger 26 and the portions of the probe 30 which are not intended for contacting tissue. Moreover, by combining the relatively small volume within the tubular extension 36 with the relatively large volume in canister 20, loss of the vacuum through out-gassing is greatly diminished.

A removable sheath 40 is received over the exterior of the probe extension 30/32 and can be attached to a proximal end of the canister 20 via a connector 42. Preferably, a heat-conductive material will be introduced into the interior of sheath 40 so that it spreads uniformly over the exterior of the probe 30/32 in order to enhance the conductivity. Preferred heat-conductive materials comprise heat-conductive powders suspended in a suitable liquid, such as diamond or graphite powders present in glycerol or other suitable carriers.

Referring now to FIGS. 2–5, the umbilical tube 16 provides a total of four fluid-conductive paths or conduits between the compressor 14 and the probe assembly 12. In particular, a low boiling point refrigerant line 50 is provided for supplying the primary refrigerant stream to the tissue-contacting surface of the probe assembly 12. A secondary refrigerant line 52 is provided for supplying high boiling point refrigerant to the heat exchanger 26, and a third line 54 is provided for supplying refrigerant for warming the probe, as described in more detail below. Refrigerant from each of the lines 50, 52, and 54 provided to the probe assembly 12 is returned from the probe assembly to the compressor 14 through the interior of the umbilical tube 16 itself. Thus, a total of four flow paths are provided.

The heat exchanger 26 comprises an outer stainless steel tube or shell 56 and an interior copper tube 58. The inner tube 58 is mounted concentrically within the shell 56 and held in place by spiral ridges 60 formed on the exterior of the copper inner tube 58. The ridges 60 define a flow path for the secondary pre-cooling refrigerant stream as described below. The combination of shell 56 and inner tube 58 is wound into the helical coil best observed in FIG. 2. The high boiling point refrigerant line 50 opens directly into the distal end of the inner tube 58, and the secondary refrigerant line 52 passes concentrically through the entire length of the inner tube 58 to its distal end, as described in more detail in connection with FIG. 6 below. The interior of inner tube 58 thus serves as a conduit for passing the primary refrigerant through the heat exchanger 26 while the annular space between the exterior of inner tube 58 and the interior of shell 56 acts as a flow path for returning expanded secondary refrigerant for cooling the heat exchanger 26. The third refrigerant line 54 passes out from the umbilical tube 16 into the interior of canister 20 and bypasses the heat exchanger 26, as best seen in FIG. 2. It will be appreciated that the refrigerant in line 54 is the "warm" fluid for warming the tissue-contacting surface of probe assembly 12, as described in more detail below. Thus, cooling of line 54 is to be avoided.

Figure 6:
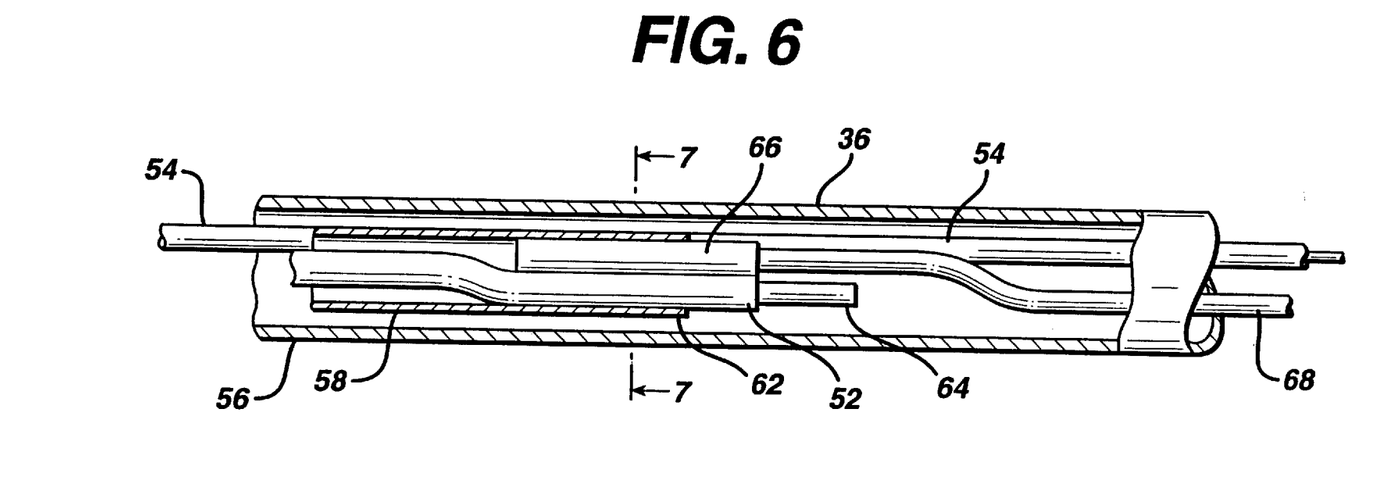
FIG. 6 is a detailed, cross-sectional view of a distal end of the heat exchanger of the probe of FIG. 2.
Figure 7:
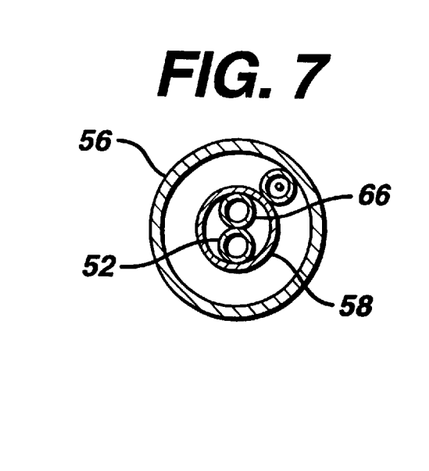
FIG. 7 is a cross-sectional view taken along line 7–7 of FIG. 6.
Figure 8:
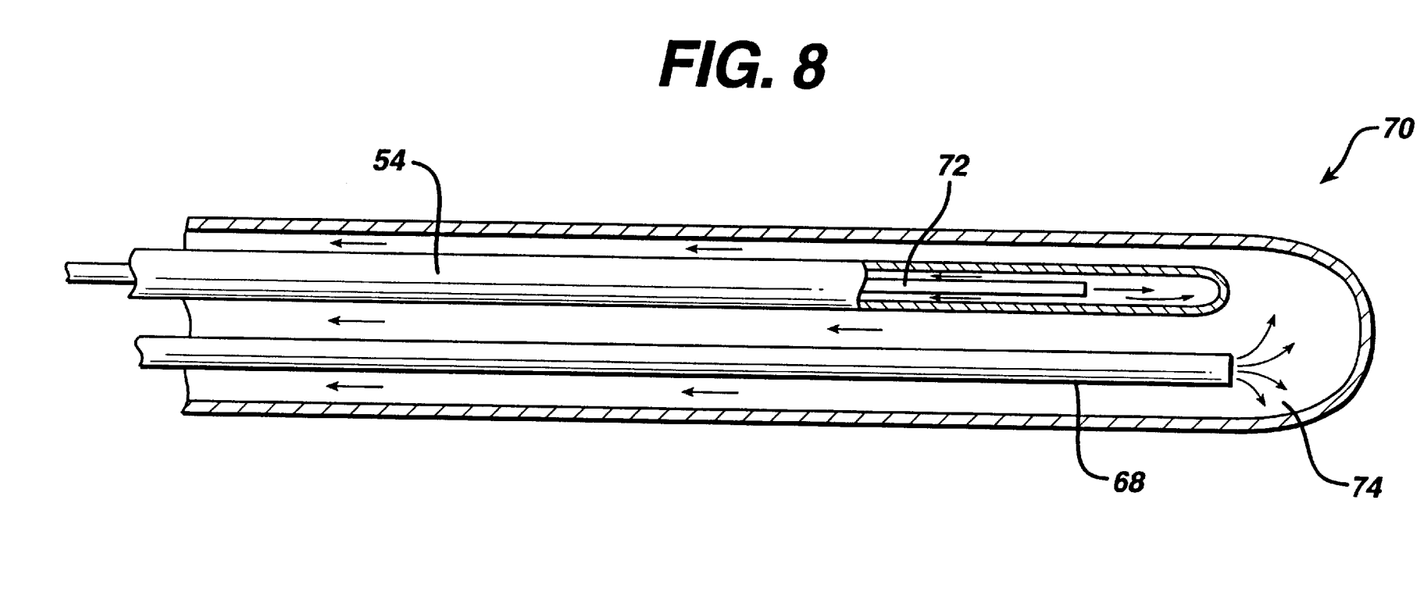
FIG. 8 is a detailed, cross-sectional view of the distal tip of the probe of FIG. 2.

Referring now to FIGS. 6 and 7, the heat exchanger 26 exits through the distal end 24 of the canister 20 and again assumes a straight configuration. At some point outside of the canister 20, warming line 54 reenters the extension 36 of the probe. The inner tube 58 terminates at a distal end 62 and the secondary refrigeration line 52 terminates in an expansion orifice 64 in the form of a capillary. Thus, a refrigerant flowing through line 52 will flow into the interior of the heat exchanger shell 56 and will flow proximally back over the exterior of the inner tube 58 to cool the tube 58. The low boiling point refrigerant which had been within the main lumen of inner tube 58 flows into a transition tube 66 and then into an expansion tube 68 which extends all the way to the tip 70 of the probe assembly 12, as best illustrated in FIG. 8. It will be appreciated that the low boiling point refrigerant that had been passing through the main lumen of inner tube 58 will have been cooled as a result of pre-cooling of the tube by the secondary refrigerant flowing from line 52. The third refrigerant line 54 (which has bypassed the main portion of the heat exchanger) will also pass through the shell 56 to the distal tip 70 of the probe assembly, as also shown in FIG. 8. The tube 54 comprises a pair of concentric tubes with the inner tube 72 passing gas into the outer tube 54 with no or partial expansion so that the tube is heated by the refrigerant flow. The return flow of refrigerant through tube 54 will eventually be recombined with the other refrigerants in the return lumen of umbilical tube 16. Thus, probe assembly 12 can be operated in a first cooling mode where the low boiling point refrigerant is expanded from the distal tip of expansion line 58, as shown by arrows 74 in FIG. 8. Alternatively, the high boiling point refrigerant flow can be terminated, and the probe tip 70 operated in a warming mode by passing a warm refrigerant through inner tube 72 into line 54 so that the refrigerant does not expand and can act to warm the probe.

Figure 9:
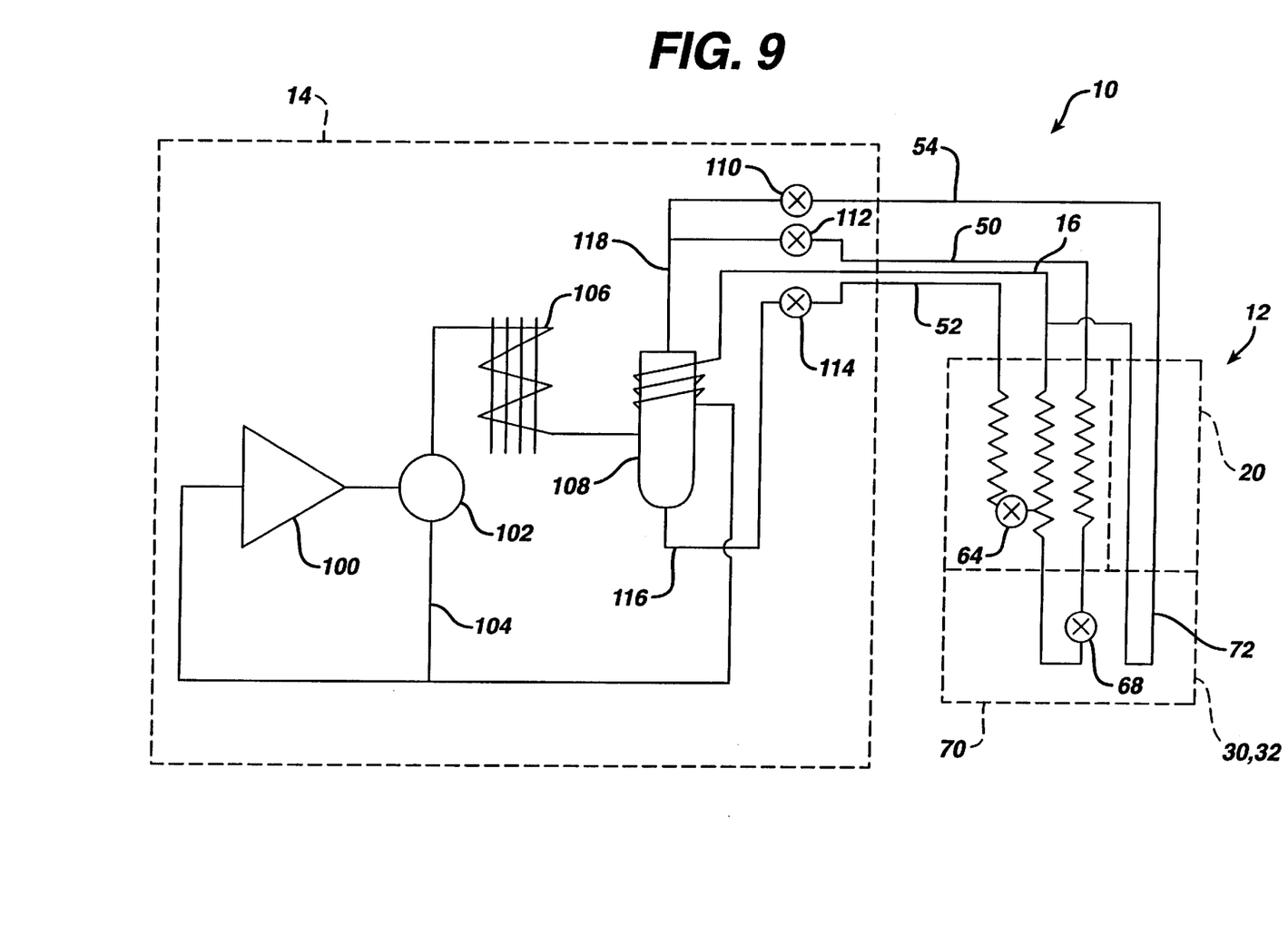
FIG. 9 is a schematic illustration of the refrigerant flow between the compressor and probe of FIG. 1.

Referring now to FIG. 9, refrigerant flow within the system 10 of the present invention will be described in general. The compressor 14 comprises a compressor unit 100, an oil separator 102, a capillary 104 that returns separated oil to the compressor unit 100, an air-cooled condenser 106, and a two-stage separator 108. Valves 110, 112, and 114 are provided to control the flow of refrigerant from the compressor 14 to the probe assembly 12. The two-stage separator 108 comprises a lower cyclone section for separating the incoming cooled, condensed refrigerant into a liquid phase which flows downward to line 116 and a vapor phase which flows upward to line 118. A portion of the upward vapor flow, however, will be condensed by returning cooled refrigerant through line 116 which is coiled around the upper section of the separator 108. Thus, the liquid refrigerant passing outward through line 116 and vapor refrigerant 118 passing upwardly through line 118 will be in equilibrium. The thermodynamics of this system are discussed in detail in U.S. Pat. Nos. 5,644,502 and 5,617,739, which have been previously incorporated herein by reference. The liquid refrigerant passes through valve 114 and line 52 into the heat exchanger and terminates in the expansion orifice/capillary 64, as described previously. Control of valve 14 determines whether or not flow of this refrigerant stream to the probe assembly 12 is established. The refrigerant vapor 118 passes either through valve 112 and through line 50 to the heat exchanger, as described previously, or through valve 110 and line 54 to the probe heating section 72, also as previously described.

Operation of the system 10 for the standby (pre-cooling) and cooling modes will now be described in connection with FIGS. 10A–10D. System 10 is pre-cooled so that the heat exchanger in canister 20 is maintained at a low temperature, preferably minus 60° C. or lower, by running the compressor to recirculate the refrigerant through air cooler 106 and into separator 108. In the pre-cooling mode, both overhead outlet valves 110 and 112 will be closed so that all flow of a refrigerant passes out through line 116, valve 114, line 52, and through the expansion orifice 64 to cool the heat exchanger. The expanded refrigerant from expansion orifice 64 will thus flow back through the heat exchanger and tube 16 and over the coils 120 and eventually back through return line 122 to the compressor unit 100. The system 10 may be operated in the standby or pre-cool mode for as long as desired and until steady state is achieved and the probe is to be contacted against tissue for therapeutic cooling.

Figure 10A:
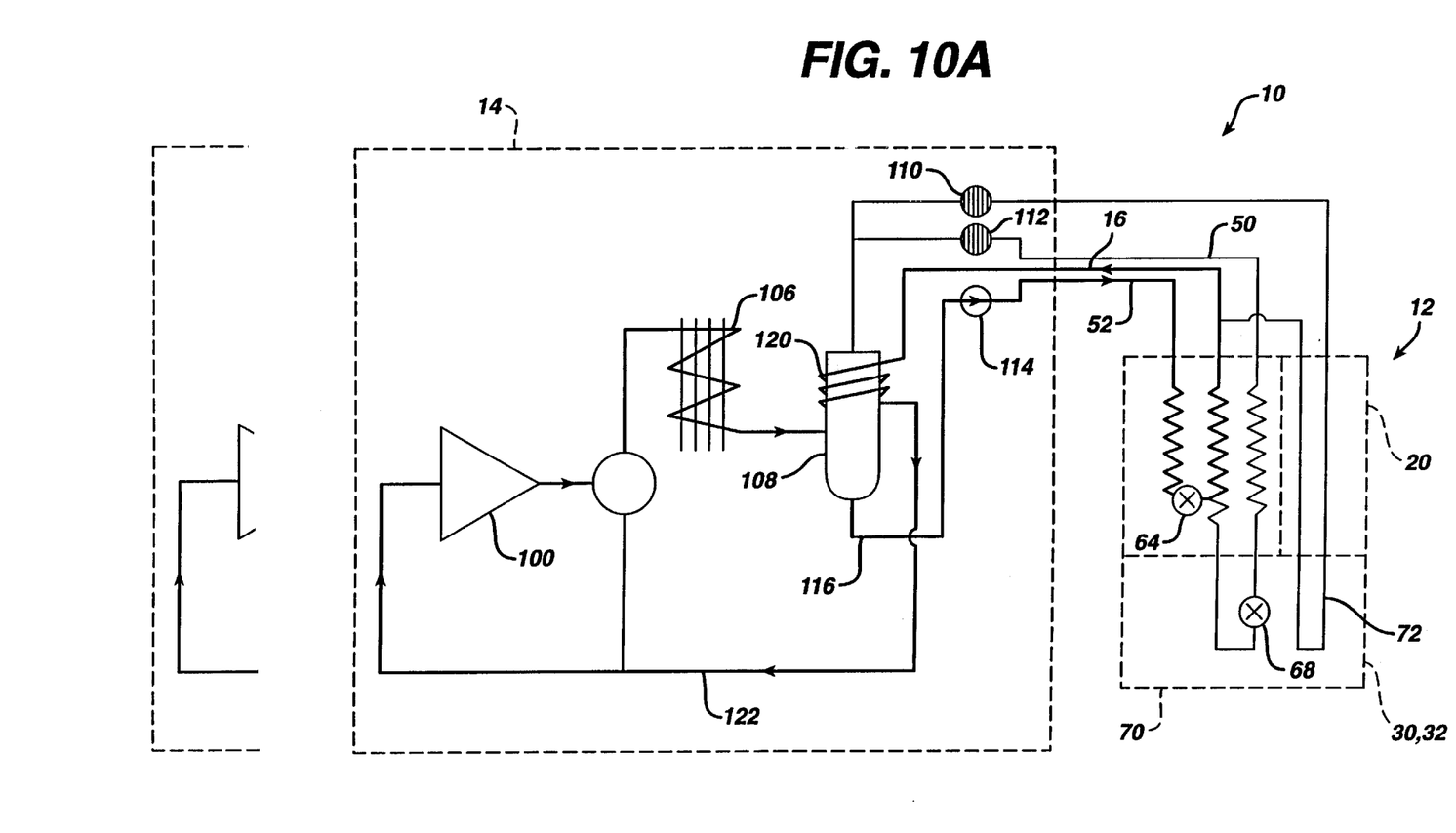
FIGS. 10A–10D illustrate the various operating modes of the system of FIG. 1.
Figure 10B:
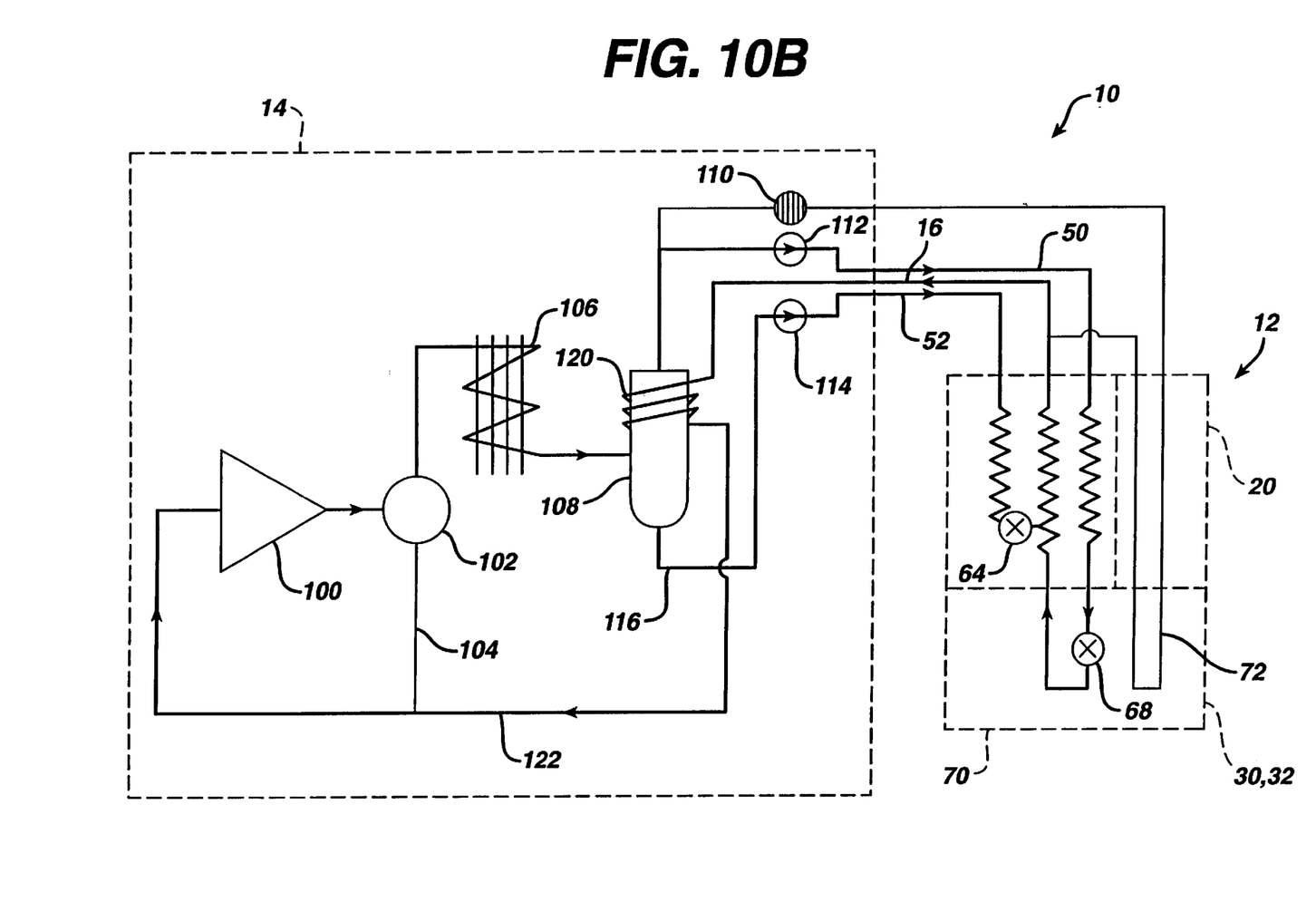

In order to cool the probe, after pre-cooling of the heat exchanger 26 has been achieved, valve 112 may be opened as illustrated in FIG. 10B. Opening of valve 112 permits the primary low boiling point refrigerant stream to pass through line 50 and expansion orifice 68 into the probe tip 70. The expansion of the refrigerant in the probe tip causes very rapid cooling, typically to a temperature at or below minus 100°C. after a very short time, typically several minutes or less. The cooled, expanded refrigerant is then passed back to the compressor unit 100 through return line 16 together with the secondary refrigerant from valve 114 and line 52.

Figure 10C:
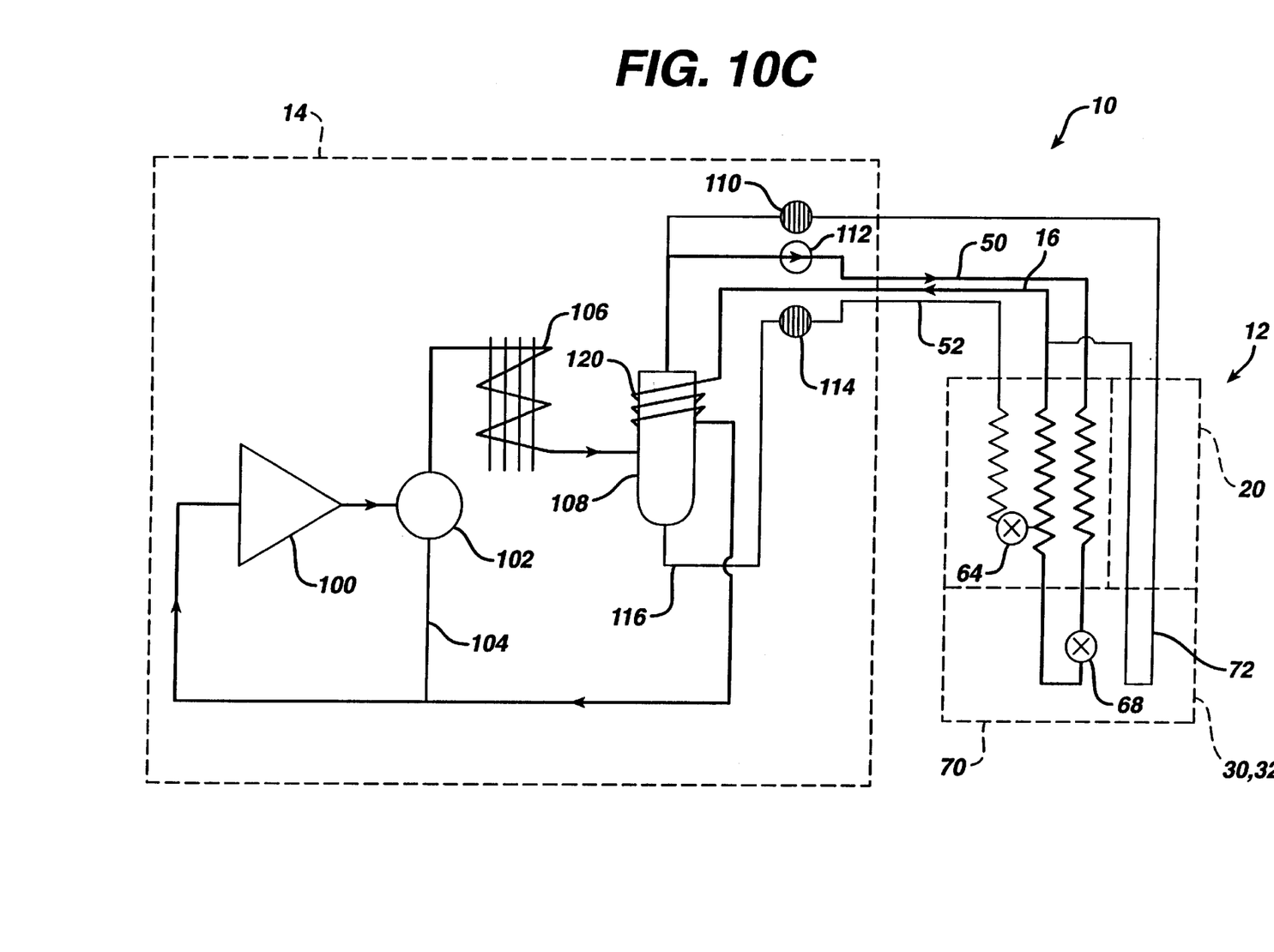

In an alternative cooling mode, the valve 112 may remain open to cool the probe tip 70, but the pre-cooling is terminated by closing valve 114, as illustrated in FIG. 10C.

Figure 10D:
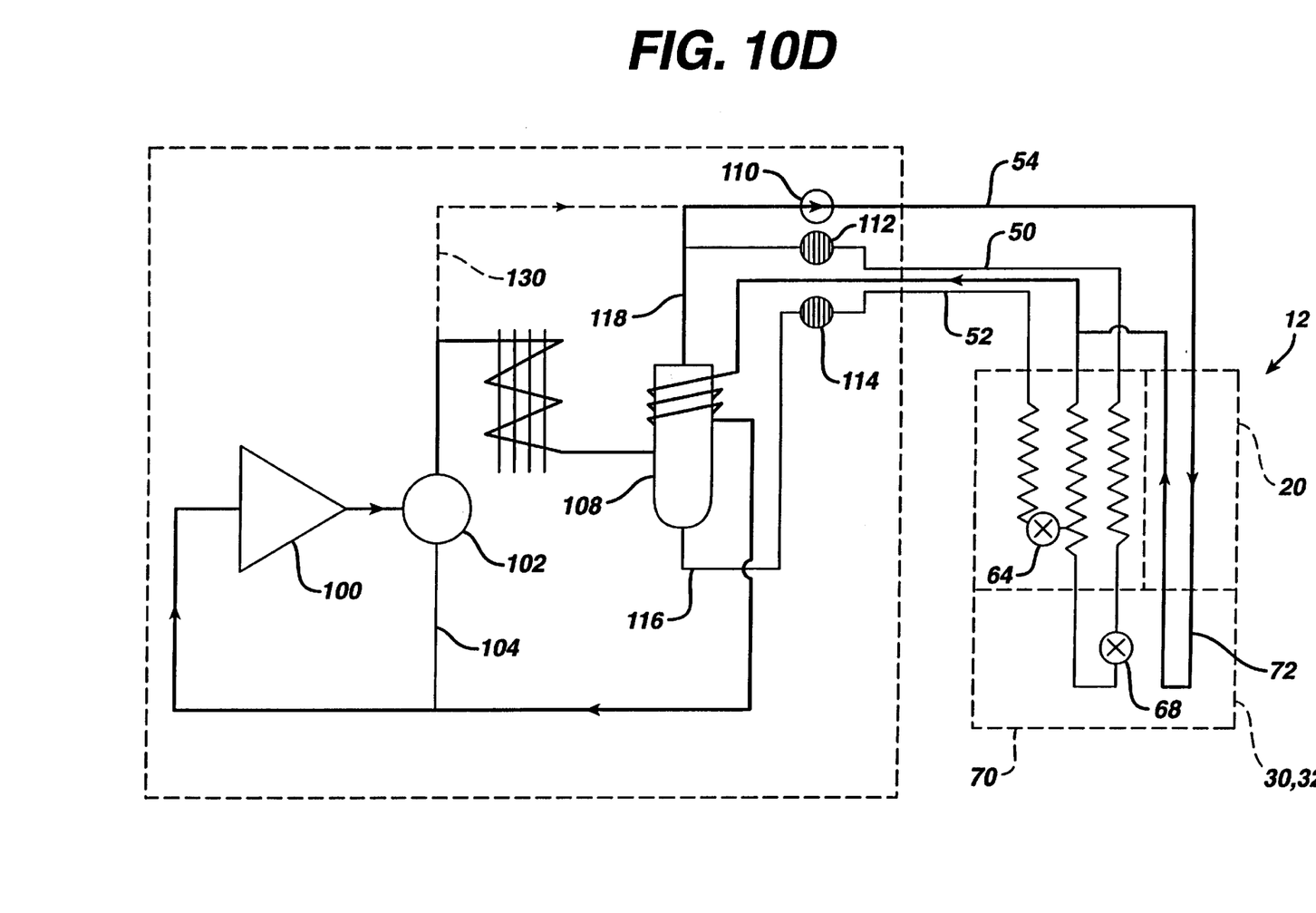

After a cycle of cooling has been completed, it is often desirable to warm the probe tip. Warming of the probe tip may be accomplished using refrigerant from overhead line 118, as illustrated in FIG. 10D. This is done by opening valve 110 and closing valves 112 and 114, as illustrated. The refrigerant from overhead line 118 is generally at about room temperature and will provide sufficient warming of the probe 70 for most purposes. If greater warming is desired, it will be possible to access the hot refrigerant after being heated by compression in the compressor unit 100 and prior to being cooled in condenser 106. This alternative flow path is shown in broken line 130 in FIG. 10D. In either case, the warm or hot refrigerant will pass through line 54 to section 72 in probe tip 70 in order to provide the desired warming. The refrigerant will then return via conduit 16 as with all other refrigerants, back to the recirculating refrigeration system of compressor 14.

The following experiments are offered by way of illustration, not by way of limitation.

EXPERIMENTAL

Figure 11:
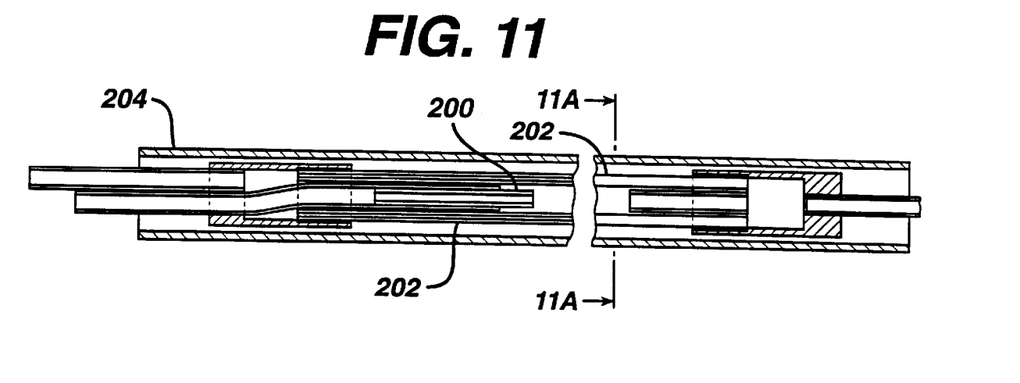
FIGS. 11, 11A and 12 illustrate a test system whose operation is described in the Experimental section.
Figure 11A:
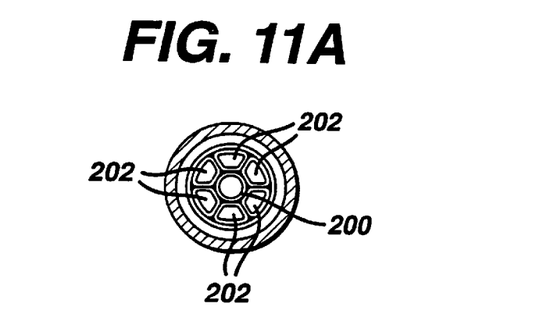
Figure 12:
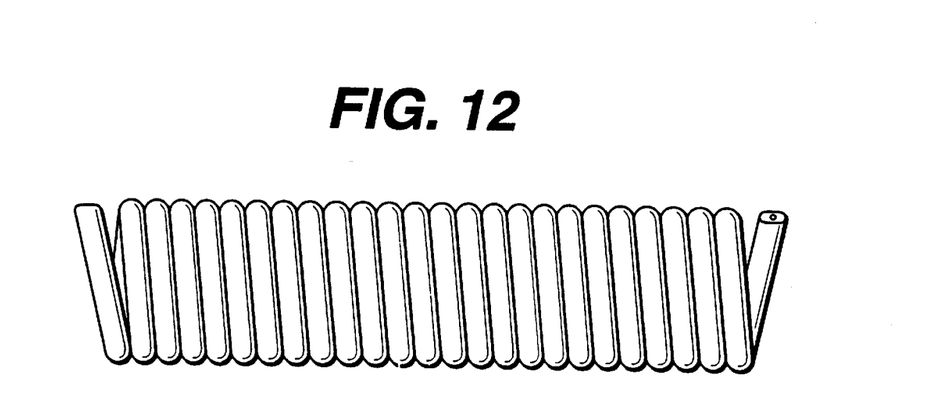

A seven tube heat exchanger, as shown in FIGS. 11, 11A, and 12 was. constructed and included a copper capillary tube 200 having an outside diameter of 1.57 mm and an inside diameter of 1.17 mm surrounded by six additional copper capillary tubes 202, each having an outside diameter of 1.02 mm and an inside diameter of 0.51 mm. The capillary tube assembly was enclosed in a stainless steel outer tube 204 having an outer diameter of 6.35 mm and an inside diameter of 5.94 mm. The entire assembly was wound into a helical coil, as shown in FIG. 12. the inner capillary tube 200 feeds liquid from a liquid-vapor separator (as described above) and terminates at a point 203.2 cm from the warm end. This defines a flow restrictor which is equivalent to orifice 64 in FIG. 9. After expansion, low pressure liquid and vapor from the termination point of capillary 200 return to a compressor through the annular space between the outer surface of the seven capillary tube assembly and the inner wall of the stainless steel tube 204.

The heat exchanger was tested with a gas mixture as follows:

| Component | Weight Fraction |
|---|---|
| Trifluoroethane | 0.211 |
| Tetrafluoromethane | 0.320 |
| HCFC123 | 0.180 |
| Argon | 0.150 |
| CHCF$_5$ | 0.126 |
| CF$_3$CH$_2$F | 0.013 |
|  | 1.000 |

A Danfloss FF10GX compressor with a 9.05 cm$^3$ displacement provided an approximately 310 cm$^3$/sec flow to the heat exchanger. The results for two freeze and one thaw cycles are shown below.

| Mode | Freeze 1 | Freeze 2 | Thaw |
| --- | --- | --- | --- |
| Low pressure, Psig | 19 | 12 | 18 |
| High pressure, Psig | 300 | 300 | 390 |
| Heat exchanger temperature, C. | −100 | −141 | −130 |
| Cold Probe temperature, C. | −127 | −127 | 37 |
| Compressor temperature, C. | 67 | 67 | 70 |
| Room temperature, C. | 22 | 22 | 22 |

While the above is a complete description of the preferred embodiments of the invention, various alternatives, modifications, and equivalents may be used. Therefore, the above description should not be taken as limiting the scope of the invention which is defined by the appended claims.

What is claimed is:

1. A cryosurgical instrument comprising:
   a) a vacuum enclosure comprising a helical coil heat exchanger;
   b) a probe of smaller diameter than the vacuum enclosure extending from the heat exchanger and terminating at its distal end with a closed tip providing a freezing zone effective during operation of the instrument to freeze living tissue when in contact therewith;
   c) a vacuum enclosure extension enclosing a portion of the probe; and
   d) a compressor for supplying a refrigerant to the heat exchanger.

2. The cryosurgical instrument of claim 1, wherein the vacuum enclosure and probe are present in a hand-held assembly.

3. The cryosurgical instrument of claim 1 further comprising a sheath adapted for removal placement over the probe and vacuum enclosure extension.

4. The cryosurgical instrument of claim 3, wherein the sheath is composed of metal.

5. The cryosurgical instrument of claim 4, further comprising a heat conductive material between an exterior surface of the probe and an interior surface of the sheath.

6. The cryosurgical instrument of claim 4, wherein the heat conductive material comprises a heat conductive powder suspended in a liquid carrier.

7. The cryosurgical instrument of claim 1 wherein the vacuum enclosure connects to the compressor through a flexible connector.

8. The cryosurgical instrument of claim 1 wherein the heat exchanger comprises an outer coiled tube with at least one coiled tube disposed within the outer coiled tube.

9. A cryosurgical instrument for ablating the endometrial lining of the uterus comprising:
   a) A hand-held assembly comprising a vacuum enclosure and a helical coil heat exchanger disposed within the vacuum enclosure;
   b) a probe of smaller diameter than the vacuum enclosure extending from the heat exchanger and terminating at its distal end with a closed tip providing a freezing zone effective during operation of the instrument to freeze living tissue when in contact therewith;
   c) a vacuum enclosure extension enclosing a portion of the probe; and
   d) a compressor for supplying a refrigerant to the heat exchanger.

10. A method of ablating the endometrial lining of the uterus comprising:
   a) providing a hand-held assembly comprising a vacuum enclosure and a helical coil heat exchanger disposed within the vacuum enclosure and a probe of smaller diameter than the vacuum enclosure and extending from the heat exchanger and terminating at the distal end of the probe a closed tip providing a freezing zone;
   b) providing a vacuum enclosure extension enclosing a portion of the probe;
   c) inserting a portion of the probe within the uterus; and
   d) compressing a refrigerant and supplying the refrigerant to the freezing zone.

* * * * *